(12) United States Patent
Cintrat et al.

(10) Patent No.: US 9,040,482 B2
(45) Date of Patent: May 26, 2015

(54) OCTAPEPTIDE COMPOUNDS AND THERAPEUTIC USE THEREOF

(75) Inventors: Jean-Christophe Cintrat, Igny (FR); Melinda Ligeti, Budapest (HU); Bernard Rousseau, Levallois-Perret (FR); Franck Artzner, Cesson Sévigné (FR); Christophe Tarabout, Montrouge (FR); Marie-Thérèse Paternostre, Verrières le Buisson (FR); Nicolas Fay, Sartrouville (FR); Roland Cherif-Cheikh, Castelldefels (ES); Céline Valery, Barcelona (ES)

(73) Assignees: IPSEN PHARMA S.A.S., Boulogne-Billancourt (FR); COMMISSARIAT A L'ENERGIE ATOMIQUE (C.E.A.), Paris (FR); CENTRE NATIONAL DE LA RECHERCHE SCIENTIFIQUE (C.N.R.S.), Paris (FR)

(*) Notice: Subject to any disclaimer, the term of this patent is extended or adjusted under 35 U.S.C. 154(b) by 0 days.

(21) Appl. No.: 13/806,510

(22) PCT Filed: Jun. 21, 2011

(86) PCT No.: PCT/FR2011/000352
§ 371 (c)(1),
(2), (4) Date: May 10, 2013

(87) PCT Pub. No.: WO2011/161332
PCT Pub. Date: Dec. 29, 2011

(65) Prior Publication Data
US 2013/0252892 A1    Sep. 26, 2013

(30) Foreign Application Priority Data

Jun. 22, 2010   (EP) ..................................... 10290336

(51) Int. Cl.
| | |
|---|---|
| C07K 14/655 | (2006.01) |
| A61K 38/31 | (2006.01) |
| A61P 5/02 | (2006.01) |
| C07K 7/54 | (2006.01) |
| A61K 38/00 | (2006.01) |

(52) U.S. Cl.
CPC . *C07K 7/54* (2013.01); *A61K 38/00* (2013.10); *C07K 14/655* (2013.01); *C07K 14/6555* (2013.01)

(58) Field of Classification Search
None
See application file for complete search history.

(56) References Cited

U.S. PATENT DOCUMENTS 5,968,903 A * 10/1999 Kaneko et al. ............... 514/2.8
6,387,932 B1 * 5/2002 Zhou et al. .................... 514/323

FOREIGN PATENT DOCUMENTS

WO    WO 2010/037930    4/2010

OTHER PUBLICATIONS

Valéry, et al. (2008) *Biophysical Journal* 94(5): 1782-1795.

*Primary Examiner* — Maury Audet
(74) *Attorney, Agent, or Firm* — Hunton & Williams LLP

(57) ABSTRACT

The present invention relates to novel octapeptide compounds of general formula (I), $$R\text{-}AA^1\text{-}cyclo(AA^2\text{-}Tyr^3\text{-}D\text{-}Trp^4\text{-}AA^5\text{-}Val^6\text{-}Cys^7)\text{-}Thr^8\text{-}NH_2 \qquad (I)$$

As these products have a good affinity for certain sub-types of somatostatin receptors, they are particularly useful for treating the pathological states or diseases in which one (or more) of the somatostatin receptors is (are) involved. The invention also relates to pharmaceutical compositions containing said products and their use for the preparation of a medicament.

18 Claims, 1 Drawing Sheet

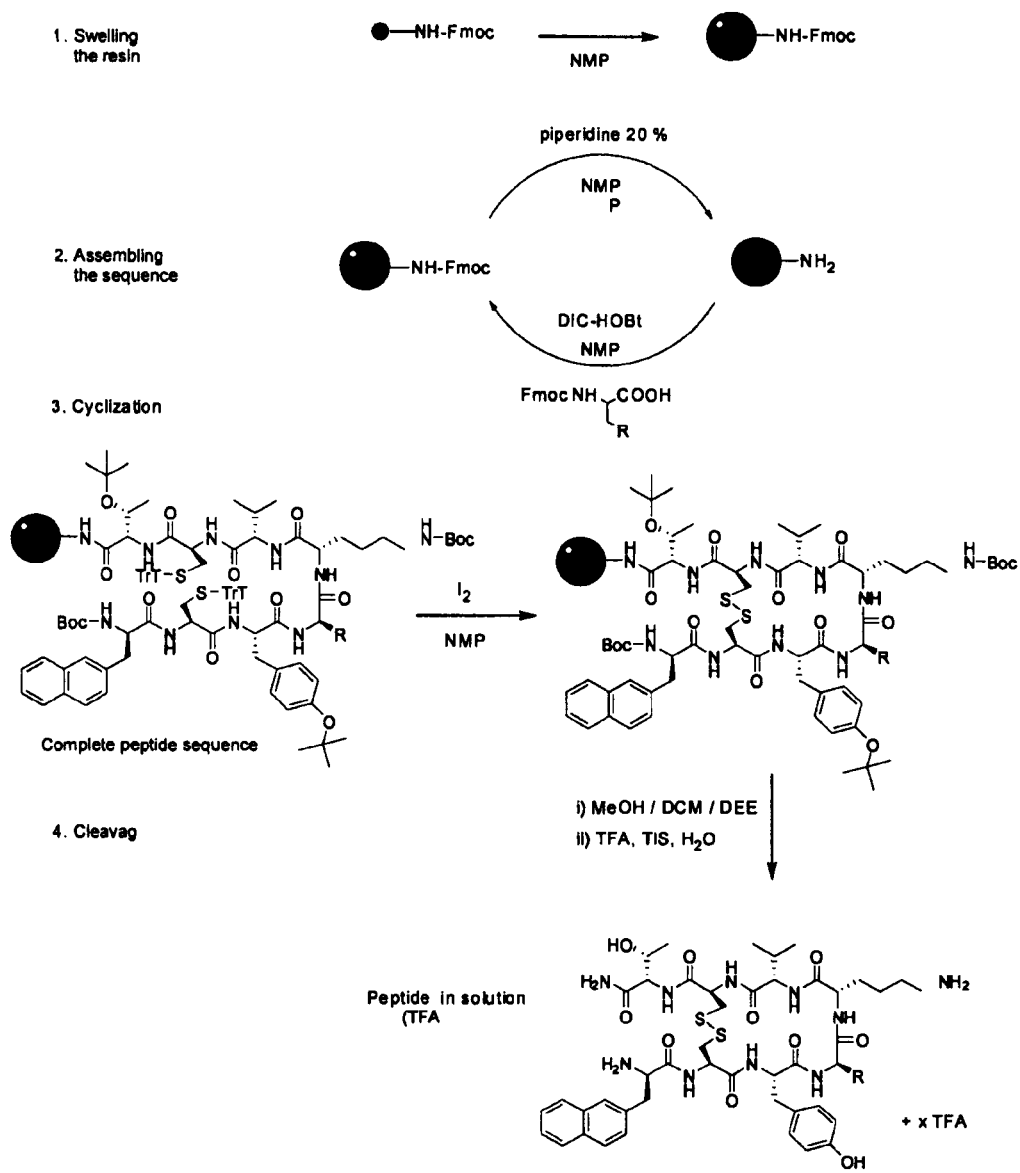

OCTAPEPTIDE COMPOUNDS AND THERAPEUTIC USE THEREOF

This application is a national stage filing of PCT/FR2011/000352, filed Jun. 21, 2011, which claims priority to EP 10290336.6, filed Jun. 22, 2010, the subject matter of which is incorporated herein in its entirety.

The present invention relates to novel octapeptide compounds. As these products have a good affinity for certain sub-types of somatostatin receptors, they are particularly useful for treating the pathological states or diseases in which one (or more) of the somatostatin receptors is (are) involved. The invention also relates to pharmaceutical compositions containing said products and their use for the preparation of a medicament.

Somatostatin (SST) is a cyclic tetradecapeptide which was isolated for the first time from the hypothalamus as a substance which inhibits the growth hormone (Brazeau P. et al., Science 1973, 179, 77-79). It also operates as a neurotransmitter in the brain (Reisine T. et al., Neuroscience 1995, 67, 777-790; Reisine et al., Endocrinology 1995, 16, 427-442). The heterogeneity of the biological functions of somatostatin and the structure-activity relationships of its peptide analogues have led to the discovery of 5 sub-types of membrane receptors (Yamada et al., Proc. Natl. Acad. Sci. U.S.A, 89, 251-255, 1992; Raynor, K. et al, Mol. Pharmacol., 44, 385-392, 1993). Molecular cloning has made it possible to show that the bioactivity of somatostatin depends directly on these five sub-types of receptors.

The functional roles of these receptors are currently being actively studied. Preferential activation of sub-types 2 and 5 has been associated with the suppression, in the adenomas secreting these hormones, of the growth hormone GH (acromegalia), the hormone TSH and prolactin; but the precise role of each sub-type remains to be determined.

Among the pathological disorders associated with somatostatin (Moreau J. P. et al., Life Sciences 1987, 40, 419; Harris A. G. et al., The European Journal of Medicine, 1993, 2, 97-105), there can be mentioned for example: acromegalia, hypophyseal adenomas, Cushing's disease, gonadotrophinomas and prolactinomas, catabolic side-effects of glucocorticoids, diabetes, diabetic retinopathy, diabetic nephropathy, hyperthyroidism, gigantism, endocrinic gastroenteropancreatic tumours including carcinoid syndrome, VIPoma, insulinoma, nesidioblastosis, hyperinsulinemia, glucagonoma, gastrinoma and Zollinger-Ellison's syndrome, GRFoma as well as acute bleeding of the oesophageal varices, gastroesophageal reflux, gastroduodenal reflux, pancreatitis, enterocutaneous and pancreatic fistulae but also diarrhoeas, refractory diarrhoeas of acquired immunodeficiency syndrome, chronic secretory diarrhoea, diarrhoea associated with irritable bowel syndrome, disorders linked with gastrin releasing peptide, secondary pathologies with intestinal grafts, portal hypertension as well as haemorrhages of the varices in patients with cirrhosis, gastro-intestinal haemorrhage, haemorrhage of the gastroduodenal ulcer, Crohn's disease, systemic scleroses, dumping syndrome, small intestine syndrome, hypotension, scleroderma and medullar thyroid carcinoma, diseases linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumours, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of H pylori, psoriasis, as well as Alzheimer's disease. Osteoporosis can also be mentioned.

These days, increasing attention is being given to peptides having an affinity for the somatostatin receptors. Thus, lanreotide has been much studied for the treatment of diseases linked to growth hormone (Cendros J M, Peraire C, Trocóniz I F, Obach R. Pharmacokinetics and population pharmacodynamic analysis of lanreotide Autogel. Metabolism. 2005 October, 54(10), 1276-81).

Octapeptide compounds consisting of the lanreotide modified in position 4 have been described in International patent application PCT/FR09/001162.

The need to find alternatives to existing solutions therefore constitutes a major challenge. The present invention comes within this context.

The applicant therefore proposes novel octapeptide compounds having a good affinity for the somatostatin receptors.

A subject of the present invention is therefore an octapeptide compound of general formula (I)

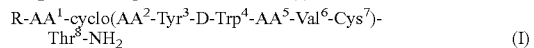

$$R\text{-}AA^1\text{-}cyclo(AA^2\text{-}Tyr^3\text{-}D\text{-}Trp^4\text{-}AA^5\text{-}Val^6\text{-}Cys^7)\text{-}Thr^8\text{-}NH_2 \quad (I)$$

in which $AA^1$ represents an amino acid radical linked to the R radical and to the amino acid $AA^2$ according to the formula

(II)

in which
R1 represents the naphthyl radical optionally substituted by one or more alkyl radicals;
R represents a hydrogen atom or an alkyl or acetyl radical;
$AA^2$ represents an amino acid radical linked to the amino acids $AA^1$ and $Tyr^3$ according to the formula

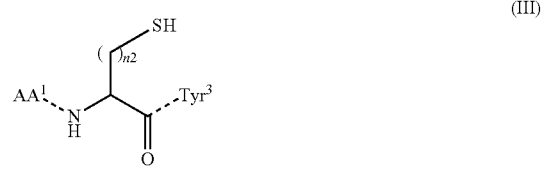

(III)

in which n2 represents an integer from 1 to 2;
$AA^5$ represents an amino acid radical linked to the amino acids $Trp^4$ and $Val^6$ according to the formula

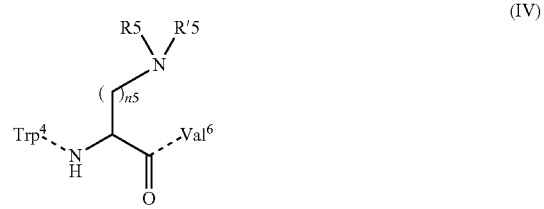

(IV)

in which R5 and R'5 represent independently a hydrogen atom or an alkyl or acetyl radical, and n5 represents an integer from 1 to 4;

it being understood that if $AA^2$ represents a cysteine amino acid radical, then either $AA^5$ represents a lysine amino acid radical and $AA^1$ does not represent a naphthylalanine amino acid radical;

or $AA^1$ represents a naphthylalanine amino acid radical and $AA^5$ does not represent a lysine amino acid radical;

or $AA^1$ does not represent a naphthylalanine amino acid radical and $AA^5$ does not represent a lysine amino acid radical;

if $AA^2$ does not represent a cysteine amino acid radical, then $AA^1$ represents a naphthylalanine amino acid radical and $AA^5$ represents a lysine amino acid radical, and it being understood that all the amino acids can be of D or L configuration, or a pharmaceutically acceptable salt of this compound.

According to the present invention, by amino acid radical is meant the radical formed by an amino acid engaged in peptide bonds by means of its amine and acid functions. Thus, an amino acid radical having X as side chain will have for radical the radical of formula —NH—CH(X)—C(O)—.

According to the present invention, the amino acids represented by their three-letter code in a general formula, or as such, or also as radicals, can be of D or L configuration, if nothing is specified.

Moreover, according to the present invention and in accordance with convention, the designation of the peptides exemplified by their amino acid sequence represented by their three-letter code, mentions the L configuration amino acids without specifying anything whilst the D amino acids are explicitly indicated by the letter D preceding the three-letter code of the amino acid considered.

Within the meaning of the present invention, unless otherwise specified, by alkyl is meant a linear or branched alkyl radical comprising 1 to 6 carbon atoms such as methyl, ethyl, propyl, isopropyl, butyl, isobutyl, tert-butyl, pentyl, or hexyl, and preferably 1 to 4 carbon atoms.

According to the present invention, the expression pharmaceutically acceptable salt defines addition salts with inorganic acids such as hydrochloride, hydrobromide, hydroiodide, sulphate, phosphate, diphosphate and nitrate or with organic acids such as acetate, maleate, fumarate, tartrate, succinate, citrate, lactate, methanesulphonate, p-toluenesulphonate, pamoate and stearate. For other examples of pharmaceutically acceptable salts, reference can be made to "Salt selection for basic drugs", Int. J. Pharm. (1986), 33, 201-217.

According to the present invention, the amino acids represent the amino acids of D or L configuration known to a person skilled in the art, represented here according to their usual nomenclature and the modified synthetic analogues on the side chains of said amino acids among which:

D-2-Nal1, Ac-D-2-Nal1, CH₃-D-2-Nal1 represent an alanine substituted at the position by a naphthyl radical respectively unsubstituted and substituted on its amine function by an acetyl or methyl radical at its position 1;

Hcy represents a homocysteine, i.e. a cysteine the side chain of which is lengthened by one methylene member;

Orn represents an ornithine, i.e. a lysine the side chain of which is shortened by one methylene member;

Dab represents diaminobutyric acid, i.e. a lysine the side chain of which is shortened by two methylene members;

Dap represents diaminopropionic acid, i.e. a lysine the side chain of which is shortened by three methylene members;

Lys(Ac) and (Me)₂Lys represent a lysine substituted on the amine function of its side chain by one or more acetyl or methyl radicals respectively.

Preferably, n5 represents an integer from 1 to 4, and even more preferentially, n5 represents an integer from 3 to 4.

Preferably, $AA^2$ represents a cysteine amino acid radical, i.e. n2 is equal to 1.

Preferably, $AA^2$ does not represent a cysteine amino acid radical, i.e. n2 is equal to 2.

Preferably, $AA^1$ does not represent a naphthylalanine amino acid radical, i.e. R represents an alkyl or acetyl radical and $AA^5$ represents a lysine amino acid radical, i.e. n5 is equal to 4 and R5 and R'5 represent hydrogen atoms.

Preferably, $AA^1$ represents a naphthylalanine amino acid radical, i.e. R represents a hydrogen atom, and $AA^5$ does not represent a lysine amino acid radical, i.e. either n5 is an integer from 1 to 3 or n5 is equal to 4 and R5 and R'5 represent an alkyl or acetyl radical.

Preferably, $AA^1$ does not represent a naphthylalanine amino acid radical, i.e. R represents an alkyl or acetyl radical, and $AA^5$ does not represent a lysine amino acid radical i.e. either n5 is an integer from 1 to 3 or n5 is equal to 4 and R5 and R'5 represent an alkyl or acetyl radical.

Preferably, $AA^1$ represents the amino acid radical chosen from 2-Nal, Ac-2-Nal and CH₃-2-Nal. Preferably, $AA^1$ is of D configuration.

Preferably, $AA^2$ represents the amino acid radical chosen from Cys and Hcy.

Preferably, $AA^5$ represents the amino acid radical chosen from Lys, Lys(Ac), Orn, (CH₃)₂Lys, Dab and Dap.

Preferably, the octapeptide compound of general formula (I) is chosen from:

H-D-2-Nal¹-cyclo(Cys²-Tyr³-D-Trp⁴-Lys(Ac)⁵-Val⁶-Cys⁷)-Thr⁸-NH₂

Ac-D-2-Nal¹-cyclo(Cys²-Tyr³-D-Trp⁴-Lys(Ac)⁵-Val⁶-Cys⁷)-Thr⁸-NH₂

H-D-2-Nal¹-cyclo(Cys²-Tyr³-D-Trp⁴-Orn⁵-Val⁶-Cys⁷)-Thr⁸-NH₂

H-D-2-Nal¹-cyclo(Cys²-Tyr³-D-Trp⁴-(Me)₂Lys⁵-Val⁶-Cys⁷)-Thr⁸-NH₂

H-D-2-Nal¹-cyclo(Hcy²-Tyr³-D-Trp⁴-Lys⁵-Val⁶-Cys⁷)-Thr⁸-NH₂

Ac-D-2-Nal¹-cyclo(Cys²-Tyr³-D-Trp⁴-Lys⁵-Val⁶-Cys⁷)-Thr⁸-NH₂

CH₃-D-2-Nal¹-cyclo(Cys²-Tyr³-D-Trp⁴-Lys⁵-Val⁶-Cys⁷)-Thr⁸-NH₂

H-D-2-Nal¹-cyclo(Cys²-Tyr³-D-Trp⁴-Dab⁵-Val⁶-Cys⁷)-Thr⁸-NH₂

H-D-2-Nal¹-cyclo(Cys²-Tyr³-D-Trp⁴-Dap⁵-Val⁶-Cys⁷)-Thr⁸-NH₂ or a pharmaceutically acceptable salt of this compound.

More preferentially, the octapeptide compound of general formula (I) is chosen from:

H-D-2-Nal¹-cyclo(Cys²-Tyr³-D-Trp⁴-Orn⁵-Val⁶-Cys⁷)-Thr⁸-NH₂;

H-D-2-Nal¹-cyclo(Cys²-Tyr³-D-Trp⁴-(Me)₂Lys⁵-Val⁶-Cys⁷)-Thr⁸-NH₂;

H-D-2-Nal¹-cyclo(Hcy²-Tyr³-D-Trp⁴-Lys⁵-Val⁶-Cys⁷)-Thr⁸-NH₂; and

Ac-D-2-Nal¹-cyclo(Cys²-Tyr³-D-Trp⁴-Lys⁵-Val⁶-Cys⁷)-Thr⁸-NH₂;

or a pharmaceutically acceptable salt of this compound.

Even more preferably, the octapeptide compound of general formula (I) is: H-D-2-Nal¹-cyclo(Hcy²-Tyr³-D-Trp⁴-Lys⁵-Val⁶-Cys⁷)-Thr⁸-NH₂ or a pharmaceutically acceptable salt of this compound.

A subject of the invention is also a medicament comprising a compound according to the invention as defined previously.

A subject of the invention is also a pharmaceutical composition comprising a compound according to the invention as defined previously and more particularly when the compound is used as active ingredient.

A subject of the invention is also a therapeutic composition comprising a compound of general formula (I) as defined previously, as active ingredient in combination with at least one pharmaceutically acceptable excipient.

A subject of the invention is also a use of an octapeptide compound of general formula (I) as defined previously in order to produce a medicament.

A subject of the invention is also a use as defined above in which the medicament is intended to treat a pathology chosen from the diseases related to the growth hormone.

Finally, the invention relates to the use of a compound as defined previously in order to produce a medicament; and preferentially a medicament intended to treat the pathologies in which one (or more) of the somatostatin receptor(s) is (are) involved, such as acromegalia, treatment of neuroendocrine tumours, diabetic retinopathy, treatment of the vessels, joints and skin; and preferentially acromegalia or treatment of neuroendocrine tumours.

DESCRIPTION OF THE FIGURES

FIG. 1: shows that regarding the octapeptide compounds, a general procedure for the synthesis of peptides is shown in four main stages: 1/Soaking the resin; 2/Coupling the amino acids; 3/Formation of the disulphide bridge and 4/Cleavage.

The therapeutic composition according to the invention can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The therapeutic composition according to the invention can also be presented in liquid form, for example, solutions, emulsions, suspensions or syrups. Appropriate liquid supports can be, for example, water, organic solvents such as glycerol or the glycols, as well as mixtures thereof, in varying proportions, in water.

The administration of a composition according to the invention can be carried out by topical, oral, parenteral route, by intramuscular, sub-cutaneous injection etc.

Unless they are defined otherwise, all the technical and scientific terms used in the present Application have the same meaning as that usually understood by an ordinary specialist in the field to which this invention belongs.

The following experimental part is presented in order to illustrate the above procedures and should in no event be considered as a limit to the scope of the invention.

EXPERIMENTAL PART

1. Description of the Syntheses

1.1 Material/Equipment Used

HPLC-MS:

The system is a Waters (2525) brand with an in-line degasser and an automated injection system (2767). The elution consists of a water and acetonitrile gradient, with 0.1% formic acid. Detection of the eluted species is carried out with a diode array (2996), an evaporative light scattering detector (ELSD) and a mass spectrometer (see hereafter). The column is of reversed-phase type, C18-grafted, model X-Bridge 100×4.6 mm with a particle size of 3.5 µm and a pore size of 13.5 nm. The flow rate is adjusted to 1 ml min-1 and the injection volume to 20 µl.

The mass spectrometer is a Waters brand Micromass ZQ. The ionization is carried out by electrospray, with a source temperature of 120° C. and a cone voltage of 20V. The sample is introduced continuously at 0.3 ml min-1. The analyzer is of quadrupole type (model ZQ2000). The spectra are recorded using Mass Lynx 4.0 software in the range of m/z 100-1000 for the organic molecules and 100-2000 for the peptides.

Preparative HPLC:

Two systems are used for the purification of peptides. The system previously described equipped with a reversed phase-type column, C18-grafted, model X-Bridge 150×19 mm with a particle size of 5 µm and a pore size of 13.5 nm. The flow rate is 17 ml min-1. The second system is a Waters 2545 which is similar to the previous one, not equipped with a mass spectrometer. The column is a Thermo Hypurity, of reversed-phase type (C18-grafted) of size 21.2×250 mm. It is eluted by a mixture of water and acetonitrile with 0.1% TFA at a flow rate of 20 ml min-1. The two preparative HPLC systems are used in isocratic mode after determination of the optimum conditions.

NMR Analyses:

The Nuclear Magnetic Resonance Analyses are carried out on a Bruker Advance 400 Ultrashield spectrometer. The analysis frequencies are 400 MHz for the proton and 100 MHz for carbon 13. The spectra are recorded at ambient temperature, the chemical shifts are expressed in ppm and the coupling constants in Hz. The multiplicity is given in the following way: s=singlet, bs=broad singlet, d=doublet, bd=broad doublet, dd=doublet of doublets, ddd=doublet of doublets of doublets, t=triplet, bt=broad triplet, q=quadruplet, dq=doublet of quadruplet, m=multiplet.

HRMS Analyses:

The exact mass measurements were carried out on a time-of-flight mass spectrometer (LCT from Micromass®, UK), provided with an electrospray source (Z-spray) in positive mode. The external reference allowing the exact mass measurement is introduced in parallel with the sample and continuously (Lockspray™ configuration). The one used here is Leucine Enkephalin which produces an [M+Na]+ ion at m/z=578.2591. The resolution of this device is 6500 and the results are given with a deviation from the theoretical mass of less than 5 mDa. The device is driven by the Masslynx 4.0® software. The sample solubilized in water is injected into a 50% water-50% methanol flow via an HPLC provided with an automatic sample changer (Alliance 2795 from Waters®, UK) at a flow rate of 200 µl min-1. The injection volume is 10 µl. The voltage of the capillary is 2800 V. The cone voltage is 40 V. The source temperature is 120° C. The desolvation temperature is 250° C. The flow rate of the desolvation gas (nitrogen) is 500 1 h-1. The flow rate of the cone gas (nitrogen) is 20 1 h-1. TDC Stop: 100 mV IR Spectrometry:

The infrared spectra of the peptides are recorded by attenuated total reflection and by Fourier transform. The device is a Bruker IFS 66 equipped with a 45° N Znse ATR module, continuously purged with nitrogen. 10 µL of solution is deposited on the crystal and thirty scans are averaged at a resolution of 4 cm-1. The signal from water is subtracted from the raw spectrum using the OPUS 4.2 software.

Freeze-Dryer:

The freeze-dryer used is a Christ Alpha 2-4 LD plus connected to a vane pump making it possible to achieve vacuums of approximately 15 μbar. The aqueous samples are solidified in the liquid nitrogen before being connected to this device.

Microscopy:

TEM of Phillips CM-20 type microscope operating at 200 kV, and SEM of Leo-Gemini type, field emission gun.

1.2 Reagents Used

The synthetic peptide resin is obtained from Novabiochem, a division of Merck Biosciences (Schwalbach, Germany). The ion exchange resin comes from the Bio-Rad laboratories (Hercules, United States).

The water used is double deionized by using a Milli-Q Plus exchange system from Millipore (Billerica, United States). The solvents for the syntheses and for the purifications are purchased from Aldrich and VWR (West Chester, United States) and, unless otherwise mentioned, are used without purification.

The amino acids are purchased from Bachem (Weil am Rhein, Germany), Fluka (Buchs, Switzerland), Acros Organics (Geel, Belgium) and NeoMPS (Strasbourg, France).

Amino Acid Precursors which are Commercially Available:

The amino acids Fmoc-Lys(Ac)—OH, Acetyl- -(2-naphthyl)-D-alanine, Fmoc-Orn(Boc)-OH, Fmoc-Homocys(Trt)-OH, Fmoc-Dab(Boc)-OH, Fmoc-Dap(Boc)-OH are commercially available.

Synthesis of the amino acid
N-Methyl-Boc-D-2-Nal-OH

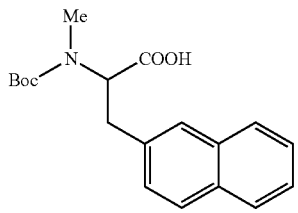 [SMILES: CN(C(=O)OC(C)(C)C)C(Cc1ccc2ccccc2c1)C(=O)O]

3.2 g of (10 mmol) of Boc-D-2-Nal-OH dissolved in 20 mL of anhydrous THF is added to a suspension of 2.4 g (60 mmol) of NaH (60% in mineral oil) in 80 mL of anhydrous THF placed at 0° C. The reaction medium is stirred for 15 minutes at 0° C. then 10 mL (160 mmol) of MeI is added dropwise. The reaction is then continued for 4 h at 0° C., 5 mL of MeI is then added, the reaction medium is then brought to ambient temperature then left under stirring overnight. The reaction medium is neutralized at 0° C. by 20 mL of a saturated solution of $NH_4Cl$ then the THF and the MeI are evaporated in a rotary evaporator. 100 mL of hexane is then added, the aqueous phase is recovered, washed twice with 100 mL of hexane. 100 mL of ethyl acetate is added and the aqueous phase is acidified (pH 2), the aqueous phase is then extracted with 3 times 100 mL of ethyl acetate. The organic phases are then combined, dried over $Na_2SO_4$, filtered then evaporated. The expected product is then crystallized from a hexane/ethyl acetate mixture (1.82 g, 55%).

$^1$H-NMR ($CD_3OD$): δ 1.22 (S, 6H, tBu), 1.27 (s, 3H, tBu), 2.72 (s, 3H, Me), 3.42-3.49 (m, 1H), 4.78 (dd, 1H, J=4.1, J=11.5), 4.97 (dd, 1H, J=4.7, J=11.5), 7.37-7.46 (m, 3H), 7.67 (s, 1H), 7.76-7.82 (m, 3H).

MS (ESI): m/z 330.0 [M+H]+

Synthesis of the amino acid Fmoc N, dimethyl lysine
(according to Int. J. Peptide Res. Ther. (2006). 12, 187-193)

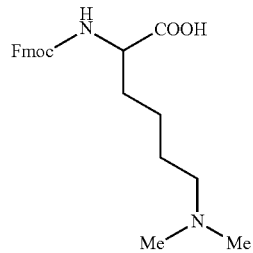

203 mg (0.5 mmol) of Fmoc-Lys-OH hydrochloride is dissolved in 10 mL of ethanol and the solution is placed at 0° C. 86 L (1.1 mmol) of formaldehyde (37% solution) is added and the mixture is maintained at 0° C. for 15 minutes. 95 mg (1.5 mmol) of $NaBH_3CN$ is then added and the reaction is continued for 15 minutes at 0° C. before adding another 86 L of formaldehyde and 95 mg of $NaBH_3CN$ and the reaction is left to proceed for 4 hours at 0° C. 10 mL of a 1N solution of HCl is added, the precipitate obtained is filtered, the solution is then taken to dryness and the compound obtained is purified by chromatography (eluent $MeOH/H_2O$ 95/5) in order to produce 110 mg of expected compound (with a very small quantity of trimethylated lysine).

$^1$H-NMR ($CD_3OD$): δ 1.4-1.9 (m, 6H); 2.7 (s, 6H); 2.91 (t, J=7.7, 2H); 4.02 (dd, J=5.3, J=7.1, 1H); 4.19 (t, J=6.8, 1H); 4.22-4.35 (m, 2H); 7.28-7.32 (m, 2H); 7.38 (t, J=7.2, 2H); 7.63-7.72 (m, 2H); 7.79 (d, J=7.5, 2H).

MS (ESI) m/z: 397.0 [M+H]+

1.3 Preparation of the Octapeptide Compounds 1.3.1 General Procedure for the Synthesis of Peptides The synthesis comprises 4 main stages:

1/Soaking the Resin:

The resin 4-(2',4'-dimethoxyphenyl-fluorenylmethoxycarbonyl-aminomethyl)-phenoxyacetamido-norleucyl-(4-methyl)-benzhydrylamine—polystyrene base—divinylbenzene (Rink Amide MBHA) is introduced into a syringe provided with a sintered glass, a tap at one end and a stopper at the other. It is filled with NMP and the mixture is placed under gentle stirring for 1 h. The solvent is then eliminated by filtration.

2/Coupling the Amino Acids:

The amino acids are coupled together in the desired order using a coupling reaction. The amino acid (2 eq) is introduced with 1-hydroxybenzotriazole (HOBt, 2.2 eq) and N,N'-diisopropylcarbodiimide (DIC, 2.2 eq) into N-methylpyrrolidinone (NMP, 5 ml/g of resin) in a test tube and stirred for a few minutes. It is then placed in the presence of the resin in its receptacle. The reaction mixture is stirred for 1 h 30 then filtered. The double coupling technique is used: the reaction mixture is filtered when the reaction has progressed by approximately 50%, and fresh reagents are reintroduced, in order to optimize the speed of reaction and the purity of the final product. The second stage consists of deprotecting the new amino acid introduced, in order to allow a new coupling. The deprotection is carried out by three treatments with piperidine in NMP (20% v/v), 5 ml/g of resin followed by three washings with NMP (10 ml/g of resin). In order to monitor the reaction, 5 µl of the filtrate corresponding to the first treatment, then 10 µl of the next two, as well as the first washing, i.e. 4 samples, are introduced into 2 ml of piperidine before measurement of the UV absorbance at 290 nm. Between each stage, three washings of the resin are carried out with NMP (10 ml/g of resin). This assembly stage therefore consists of two reactions: the coupling reaction of the amino acids and the deprotection reaction of the Fmoc group, to be carried out iteratively until the peptide sequence is complete.

3/Formation of the Disulphide Bridge:

Once the sequence is assembled, the peptide must be cyclized by the formation of the disulphide bridge. The disulphide bridge is formed by three treatments with diiodine 1 eq in NMP (5 ml/g of resin) for 2 min, 3 min and 5 min respectively. The resin is then washed 5 times with DCM and 5 times with NMP in order to eliminate the excess iodine retained in the resin (10 ml/g of resin).

4/Cleavage:

The resin must be prepared for the cleavage by two washings with NMP, two washings with methanol (MeOH), two washings with dichloromethane (DCM) and two washings with diethyl ether (DEE) (10 ml per gram of resin). The resin is then placed under vacuum for one day. The cleavage is carried out in a glass flask provided with a magnetic stirrer. The reaction mixture is formed from trifluoroacetic acid (TFA, 10 ml/g of resin) as well as triisopropylsilane (TIS) and water (3% and 2% v/v). The reaction is stirred for 4 h at ambient temperature. The medium is then filtered on sintered glass and the solid is washed twice with TFA. The filtrate is then evaporated in order to obtain a very thick white liquid. This is dissolved in a water-acetonitrile mixture 1:1 in order to be freeze-dried. After this stage, the peptide is present in the form of trifluoroacetate salt.

1.3.2 Purification

Purification is carried out by preparative high performance liquid chromatography (HPLC). The stationary phase is called "reversed" as it is grafted with $C_{18}$ alkyl chains. The mobile phase is constituted by a fixed mixture (isocratic) of water and acetonitrile with 0.1% of TFA or 1% of formic acid serving to neutralize the residual non-grafted silanols which may exist on the stationary phase.

The peptide must be dissolved in a water-acetonitrile mixture in order to be injected into the preparative HPLC. A solubility study is first carried out on a small quantity. It allows the optimum percentage of acetonitrile and the maximum quantity of peptide to be established. The lowest possible percentage of acetonitrile with a very high concentration of peptide and a resultant clear solution constitute ideal conditions.

After purification, the fractions containing the purified peptide are combined and evaporated under vacuum. The pure peptide is then recovered in large quantities of solvent to be evaporated before proceeding to freeze-drying. The peptide is in general present in the form of trifluoroacetate salt which must be exchanged by an acetate before physicochemical analysis.

1.3.3 Ion Exchange

The exchange is carried out on a strong anion exchange type resin (AG1-X8 Biorad). 245 mg of this resin are firstly washed three times with 10 ml of 1.6 N acetic acid then three times with 10 ml of 0.16 M acetic acid. 20 mg of peptide as TFA salt is then introduced into 4 ml of water and the receptacle is stirred rotatively for 1 h. The liquid is then filtered and the resin washed twice with 1 ml of distilled water. The fractions are combined then freeze-dried.

1.4 Examples

The products have been characterized according to the standard methods known to a person skilled in the art described previously.

Example 1

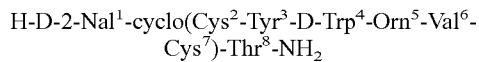

H-D-2-Nal$^1$-cyclo(Cys$^2$-Tyr$^3$-D-Trp$^4$-Orn$^5$-Val$^6$-Cys$^7$)-Thr$^8$-NH$_2$ The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys (Trt)-OH then Fmoc-L-Val-OH then Fmoc-L-Orn(Boc)-OH then Fmoc-D-Trp-OH then Fmoc-L-Tyr(tBu)-OH then Fmoc-L-Cys(Trt)-OH and finally Boc- -(2-naphthyl)-D-Ala-OH.

The compound is cyclized by the formation of a disulphide bridge, then the resin is cleaved, purified, and finally obtained in the form of acetate according to the procedure described previously in order to produce the compound H-D-2-Nal$^1$-cyclo(Cys$^2$-Tyr$^3$-D-Trp$^4$-Orn$^5$-Val$^6$-Cys$^7$)-Thr$^8$-NH$_2$.

HPLC: rt=8.65 min

HRMS (H$_2$O) m/z=1082.46102 [M+H]$^+$ (calc. 1082.45866)

$^1$H NMR (400 Mhz, D$_2$O): 0.3-0.44 (m, 1H); 0.49-0.64 (m, 1H); 0.76 (d, J=8, 3H); 0.78 (d, J=7, 3H); 1-1.12 (m, 1H); 1.06 (d, J=6.5, 3H); 1.45-1.57 (m, 1H); 1.94-2.07 (m, 1H); 2.31 (dd, J=4, J=14.7, 1H); 2.36-2.5 (m, 3H); 2.54-2.68 (m, 2H); 2.77 (d, J=7.5, 2H); 2.82-2.95 (m, 2H); 3.19 (dd, J=9, J=13.6, 1H); 3.33 (dd, J=6, J=13.6, 1H); 3.74 (dd, J=4, J=10.8, 1H); 3.82 (d, J=9.6, 1H); 4.04-4.14 (m, 2H); 4.17 (d, J=3.8, 1H); 4.24 (dd, J=6, J=8.7, 1H); 4.49 (t, J=7.5, 1H); 4.61-4.76 (m, 3H); 6.69 (d, J=8.5, 2H); 6.97 (d, J=8.5, 2H); 6.97-7.05 (m, 2H); 7.1 (bt, J=7.5, 1H); 7.29-7.45 (m, 4H); 7.65 (bs, 1H); 7.72-7.81 (m, 3H).

Example 2

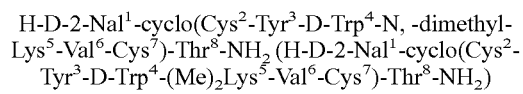

H-D-2-Nal$^1$-cyclo(Cys$^2$-Tyr$^3$-D-Trp$^4$-N, -dimethyl-Lys$^5$-Val$^6$-Cys$^7$)-Thr$^8$-NH$_2$ (H-D-2-Nal$^1$-cyclo(Cys$^2$-Tyr$^3$-D-Trp$^4$-(Me)$_2$Lys$^5$-Val$^6$-Cys$^7$)-Thr$^8$-NH$_2$)

The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys (Trt)-OH then Fmoc-L-Val-OH then Fmoc-(Me)$_2$Lys-OH then Fmoc-D-Trp-OH then Fmoc-L-Tyr(tBu)-OH then Fmoc-L-Cys(Trt)-OH and finally Boc- -(2-naphthyl)-D-Ala-OH.

The compound is cyclized by the formation of a disulphide bridge, then the resin is cleaved, purified, and finally obtained in the form of acetate according to the procedure described previously in order to produce the compound H-D-2-Nal$^1$-cyclo(Cys$^2$-Tyr$^3$-D-Trp$^4$-N dimethyl-Lys$^5$-Val$^6$-Cys$^7$)-Thr$^8$-NH$_2$.

HPLC: rt=10.48 min

HRMS (H$_2$O) m/z=1124.50620 [M+H]$^+$ (calc. 1124.50561)

$^1$H NMR (400 Mhz, D$_2$O): −0.03-0.1 (m, 1H); 0.17-0.31 (m, 1H); 0.76 (d, J=7.2, 3H); 0.78 (d, J=7, 3H); 0.97-1.18 (m, 3H); 1.07 (d, J=6.3, 3H); 1.38-1.51 (m, 1H); 1.95-2.07 (m, 1H); 2.25-2.33 (m, 1H); 2.36-2.69 (m, 5H); 2.63 (s, 6H); 2.78 (bd, J=7.3, 2H); 2.78-2.95 (m, 2H); 3.13 (dd, J=9.5, J=12.8, 1H); 3.27 (dd, J=5.9, J=13.3, 1H); 3.7 (dd, J=2.1, J=9.9, 1H); 3.81 (d, J=9.6, 1H); 4.05-4.16 (m, 3H); 4.18 (d, J=3.6, 1H); 4.5 (t, J=7.5, 1H); 4.64-4.73 (m, 3H); 6.7 (d, J=8.4, 2H); 6.95-7.05 (m, 4H); 7.1 (t, J=7.5, 1H); 7.33 (t, J=8.4, 2H); 7.36-7.45 (m, 3H); 7.63 (bs, 1H); 7.70-7.75 (m, 1H); 7.77 (d, J=8.6, 1H).

Example 3

N-Methyl-D-2-Nal$^1$-cyclo(Cys$^2$-Tyr$^3$-D-Trp$^4$-Lys$^5$-Val$^6$-Cys$^7$)-Thr$^8$-NH$_2$ (CH$_3$-D-2-Nal$^1$-cyclo(Cys$^2$-Tyr$^3$-D-Trp$^4$-Lys$^5$-Val$^6$-Cys$^7$)-Thr$^8$-NH$_2$)

The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys (Trt)-OH then Fmoc-L-Val-OH then Fmoc-L-Lys(Boc)-OH then Fmoc-D-Trp-OH then Fmoc-L-Tyr(tBu)-OH then Fmoc-L-Cys(Trt)-OH and finally Boc-N-Methyl-D-(2-naphthyl)-Ala-OH.

The compound is cyclized by the formation of a disulphide bridge, then the resin is cleaved, purified, and finally obtained in the form of acetate according to the procedure described previously in order to produce the compound N-Methyl-D-2-Nal$^1$-cyclo(Cys$^2$-Tyr$^3$-D-Trp$^4$-Lys$^5$-Val$^6$-Cys$^7$)-Thr$^8$-NH$_2$.

HPLC: rt=8.83 min
HRMS (H$_2$O) m/z=1110.48991 [M+H]$^+$ (calc. 1110.48996)

$^1$H NMR (400 Mhz, D$_2$O): −0.05-0.1 (m, 1H); 0.2-0.32 (m, 1H); 0.76 (d, J=6.4, 3H); 0.78 (d, J=6.4, 3H); 0.94-1.16 (m, 3H); 1.08 (d, J=6.4, 3H); 1.35-1.48 (m, 1H); 1.96-2.09 (m, 1H); 2.16 (dd, J=3.8, J=14.8, 1H); 2.35 (dd, J=9.3, J=14.8, 1H); 2.39-2.64 (m, 4H); 2.52 (s, 3H); 2.69-2.96 (m, 4H); 3.16 (dd, J=10.2, J=13.3, 1H); 3.38 (dd, J=5, J=13.3, 1H); 3.65 (dd, J=3.5, J=11, 1H); 3.78 (d, J=9.8, 1H); 4.06-4.19 (m, 3H); 4.22 (d, J=4, 1H); 4.5 (t, J=7.6, 1H); 4.55-4.75 (m, 3H); 6.68 (d, J=8.5, 2H); 6.95-7.03 (m, 3H); 7.09 (t, J=7.2, 1H); 7.29 (dd, J=1.3, J=8.4, 1H); 7.33 (d, J=8.2, 1H); 7.37-7.44 (m, 3H); 7.62 (bs, 1H); 7.68-7.73 (m, 1H); 7.75-7.8 (m, 2H).

Example 4

H-D-2-Nal$^1$-cyclo(Cys$^2$-Tyr$^3$-D-Trp$^4$-Dab$^5$-Val$^6$-Cys$^7$)-Thr$^8$-NH$_2$ The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys (Trt)-OH then Fmoc-L-Val-OH then Fmoc-Dab(Boc)-OH then Fmoc-D-Trp-OH then Fmoc-L-Tyr(tBu)-OH then Fmoc-L-Cys(Trt)-OH and finally Boc- -(2-naphthyl)-D-Ala-OH.

The compound is cyclized by the formation of a disulphide bridge, then the resin is cleaved, purified, and finally obtained in the form of acetate according to the procedure described previously in order to produce the compound H-D-2-Nal$^1$-cyclo(Cys$^2$-Tyr$^3$-D-Trp$^4$-Dab$^5$-Val$^6$-Cys$^7$)-Thr$^8$-NH$_2$.

HPLC: rt=8.68 min
HRMS (H$_2$O) m/z=1068.44355 [M+H]$^+$ (calc. 1068.44301)

$^1$H NMR (400 Mhz, D$_2$O): 0.76 (d, J=6.7, 3H); 0.77 (d, J=6.7, 3H); 1.06 (d, J=6.4, 3H); 1.21-1.36 (m, 1H); 1.37-1.47 (m, 1H); 1.78-1.9 (m, 2H); 1.96-2.08 (m, 1H); 2.34 (dd, J=3.8, J=14.8, 1H); 2.46 (dd, J=9.7, J=14.8, 1H); 2.54-2.68 (m, 2H); 2.78 (d, J=7.4, 2H); 2.91 (d, J=8.3, 2H); 3.16 (dd, J=9.2, J=13.5, 1H); 3.29 (dd, J=5.6, J=13.5, 1H); 3.82 (d, J=9.8, 1H); 3.86 (dd, J=3.2, J=11, 1H); 4.03-4.13 (m, 2H); 4.13-4.21 (m, 2H); 4.49 (t, J=7.4, 1H); 4.63-4.78 (m, 3H); 6.69 (d, J=8.4, 2H); 6.97 (d, J=8.5, 2H); 6.99-7.06 (m, 2H); 7.11 (t, J=7.5, 1H); 7.35 (dd, J=1, J=8.5, 1H); 7.37 (d, J=8.2, 1H); 7.38-7.44 (m, 2H); 7.65 (bs, 1H); 7.70-7.82 (m, 3H).

Example 5

H-D-2-Nal$^1$-cyclo(Cys$^2$-Tyr$^3$-D-Trp$^4$-Dap$^5$-Val$^6$-Cys$^7$)-Thr$^8$-NH$_2$ The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys (Trt)-OH then Fmoc-L-Val-OH then Fmoc-Dap(Boc)-OH then Fmoc-D-Trp-OH then Fmoc-L-Tyr(tBu)-OH then Fmoc-L-Cys(Trt)-OH and finally Boc-1-(2-naphthyl)-D-Ala-OH, The compound is cyclized by the formation of a disulphide bridge, then the resin is cleaved, purified, and finally obtained in the form of acetate according to the procedure described previously in order to produce the compound H-D-2-Nal$^1$-cyclo(Cys$^2$-Tyr$^3$-D-Trp$^4$-Dap$^5$-Val$^6$-Cys$^7$)-Thr$^8$-NH$_2$.

HPLC: rt=8.65 min
HRMS (H$_2$O) m/z=1054.42780 [M+H]$^+$ (calc, 1054.42736)

$^1$H NMR (400 Mhz, D$_2$O): 0.76 (d, J=6.7, 3H); 0.77 (d, J=6.7, 3H); 1.06 (d, J=6.4, 3H); 1.21-1.36 (m, 1H); 1.37-1.47 (m, 1H); 1.78-1.9 (m, 2H); 1.96-2.08 (m, 1H); 2.34 (dd, J=3.8, J=14.8, 1H); 2.46 (dd, J=9.7, J=14.8, 1H); 2.54-2.68 (m, 2H); 2.78 (d, J=7.4, 2H); 2.91 (d, J=8.3, 2H); 3.16 (dd, J=9.2, J=13.5, 1H); 3.29 (dd, J=5.6, J=13.5, 1H); 3.82 (d, J=9.8, 1H); 3.86 (dd, J=3.2, J=11, 1H); 4.03-4.13 (m, 2H); 4.13-4.21 (m, 2H); 4.49 (t, J=7.4, 1H); 4.63-4.78 (m, 3H); 6.69 (d, J=8.4, 2H); 6.97 (d, J=8.5, 2H); 6.99-7.06 (m, 2H); 7.11 (t, J=7.5, 1H); 7.35 (dd, J=1, J=8.5, 1H); 7.37 (d, J=8.2, 1H); 7.38-7.44 (m, 2H); 7.65 (bs, 1H); 7.70-7.82 (m, 3H).

Example 6

H-D-2-Nal$^1$-cyclo(Cys$^2$-Tyr$^3$-D-Trp$^4$-N—Ac-Lys$^5$-Val$^6$-Cys$^7$)-Thr$^8$-NH$_2$ (H-D-2-Nal$^1$-cyclo(Cys$^2$-Tyr$^3$-D-Trp$^4$-Lys(Ac)$^5$-Val$^6$-Cys$^7$)-Thr$^8$-NH$_2$)

The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys (Trt)-OH then Fmoc-L-Val-OH then Fmoc-Lys(Ac)—OH then Fmoc-D-Trp-OH then Fmoc-L-Tyr(tBu)-OH then Fmoc-L-Cys(Trt)-OH and finally Boc-1-(2-naphthyl)-D-Ala-OH, The compound is cyclized by the formation of a disulphide bridge, then the resin is cleaved, purified, and finally obtained in the form of acetate according to the procedure described previously in order to produce the compound H-D-2-Nal¹-cyclo(Cys²-Tyr³-D-Trp⁴-N—Ac-Lys⁵-Val⁶-Cys⁷)-Thr⁸-NH₂.

HPLC: rt=10.58 min
HRMS (H₂O) m/z=1138.4886 [M+H]⁺ (calc, 1138.4854)
¹H NMR (400 Mhz, D₂O/CD₃CN): 0.45-0.59 (m, 1H); 0.62-0.73 (m, 1H); 1.10 (d, J=6.7, 3H); 1.13 (d, J=6.7, 3H); 1.3-1.45 (m, 3H); 1.36 (d, J=6.4, 3H); 1.7-1.82 (m, 1H); 2.07 (s, 3H); 2.35-2.45 (m, 1H); 2.87 (d, J=6.9, 1H); 3-3.28 (m, 4H); 3.54 (d, J=7.1, 1H); 4.08 (dd, J=3.1, J=10.7, 1H); 4.19 (d, J=9.4, 1H); 4.37-4.47 (m, 2H); 4.5 (d, J=3.4, 1H); 4.75-4.8 (m, 2H); 5.25-5.29 (m, 2H); 6.99 (d, J=8.4, 2H); 7.26-7.39 (m, 5H); 7.63 (d, J=8.1, 1H); 7.67-7.76 (m, 4H); 8 (s, 1H); 8.07-8.12 (m, 3H).

Example 7

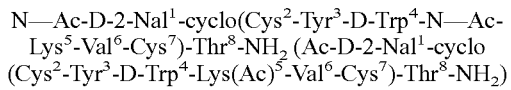

N—Ac-D-2-Nal¹-cyclo(Cys²-Tyr³-D-Trp⁴-N—Ac-Lys⁵-Val⁶-Cys⁷)-Thr⁸-NH₂ (Ac-D-2-Nal¹-cyclo(Cys²-Tyr³-D-Trp⁴-Lys(Ac)⁵-Val⁶-Cys⁷)-Thr⁸-NH₂)

The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys(Trt)-OH then Fmoc-L-Val-OH then Fmoc-Lys(Ac)—OH then Fmoc-D-Trp-OH then Fmoc-L-Tyr(tBu)-OH then Fmoc-L-Cys(Trt)-OH and finally Ac-1-(2-naphthyl)-D-Ala-OH, The compound is cyclized by the formation of a disulphide bridge, then the resin is cleaved, purified, and finally obtained in the form of acetate according to the procedure described previously in order to produce the compound N—Ac-D-2-Nal¹-cyclo(Cys²-Tyr³-D-Trp⁴-N—Ac-Lys⁵-Val⁶-Cys⁷)-Thr⁸-NH₂.

HPLC: rt=12.75 min
HRMS (H₂O) m/z=1202.4800 [M+Na]⁺ (calc, 1202.4779)
¹H NMR (400 Mhz, D₂O/CD₃CN): 0.28-0.40 (m, 1H); 0.41-0.58 (m, 1H); 0.86 (d, J=6.7, 3H); 0.89 (d, J=6.7, 3H); 1.13 (d, J=6.4, 3H); 1.55-1.65 (m, 1H); 1.81 (s, 3H); 1.85 (s, 3H); 2.16-2.22 (m, 1H); 2.73-2.94 (m, 7H); 3-3.07 (m, 1H); 3.29 (dd, J=5.7, J=13.8, 1H); 3.89 (dd, J=3.1, J=11, 1H); 4 (d, J=9.3, 1H); 4.13-4.22 (m, 2H); 4.24 (d, J=3.8, 1H); 4.53 (dd, J=6.9, J=8, 1H); 4.77 (dd, J=5.7, J=8.9, 1H); 5.22 (dd, J=4.7, J=9.6, 1H); 5.29 (dd, J=7.3, J=7.9, 1H); 6.69 (d, J=8.4, 2H); 6.99-7.11 (m, 5H); 7.36 (d, J=8, 1H); 7.41-7.49 (m, 4H); 7.73-7.82 (m, 4H), Example 8

H-D-2-Nal¹-cyclo(HomoCys²-Tyr³-D-Trp⁴-Lys⁵-Val⁶-Cys⁷)-Thr⁸-NH₂ (H-D-2-Nal¹-cyclo(Hcy²-Tyr³-D-Trp⁴-Lys⁵-Val⁶-Cys⁷)-Thr⁸-NH₂)

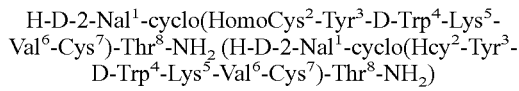

The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-Trp-OH then Fmoc-L-Tyr(tBu)-OH then Fmoc-L-HomoCys(Trt)-OH and finally Boc- -(2-naphthyl)-D-Ala-OH, The compound is cyclized by the formation of a disulphide bridge, then the resin is cleaved, purified, and finally obtained in the form of acetate according to the procedure described previously in order to produce the compound H-D-2-Nal1-cyclo(HomoCys2-Tyr3-D-Trp-4-Lys5-Val6-Cys7)-Thr8-NH2.

HPLC: rt=10.27 min
HRMS (H₂O) m/z=1132.4719 [M+Na]⁺ (calc, 1132.4749)
¹H NMR (400 Mhz, D₂O): 0.29-0.45 (m, 1H); 0.46-0.56 (m, 1H); 0.79 (d, J=6.7, 3H); 0.82 (d, J=6.7, 3H); 1.08 (d, J=6.4, 3H); 1.15-1.63 (m, 5H); 1.92-2.06 (m, 1H); 2.49-2.62 (m, 2H); 2.65-2.91 (m, 5H); 3.08 (dd, J=11.1, J=12.8, 2H); 3.21 (s, 1H); 3.37 (dd, J=5.1, J=13, 2H); 3.74 (d, J=9.3, 2H); 3.92 (dd, J=4.1, J=9.6, 2H); 4.5-4.21 (m, 6H); 4.25 (d, J=3.9, 2H); 4.42 (dd, J=6.5, J=8.8, 2H); 4.56 (dd, J=5.3, J=9.3, 2H); 6.68 (d, J=8.5, 2H); 6.91-7.12 (m, 5H); 7.29-7.44 (m, 5H); 7.62 (s, 1H); 7.75-7.83 (m, 3H).

Example 9

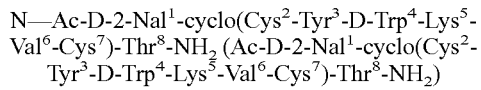

N—Ac-D-2-Nal¹-cyclo(Cys²-Tyr³-D-Trp⁴-Lys⁵-Val⁶-Cys⁷)-Thr⁸-NH₂ (Ac-D-2-Nal¹-cyclo(Cys²-Tyr³-D-Trp⁴-Lys⁵-Val⁶-Cys⁷)-Thr⁸-NH₂)

The open peptide is obtained according to the protocol described previously by the succession of coupling, deprotection of the Fmoc (9-fluorenylmethyloxycarbonyl) group and coupling of the following amino acid on solid support in the following order: Fmoc-L-Thr(tBu)-OH then Fmoc-L-Cys(Trt)-OH then Fmoc-L-Val-OH then Fmoc-L-Lys(Boc)-OH then Fmoc-D-Trp-OH then Fmoc-L-Tyr(tBu)-OH then Fmoc-L-Cys(Trt)-OH and finally Ac- -(2-naphthyl)-D-Ala-OH, The compound is cyclized by the formation of a disulphide bridge, then the resin is cleaved, purified, and finally obtained in the form of acetate according to the procedure described previously in order to produce the compound N—Ac-D-2-Nal¹-cyclo(Cys²-Tyr³-D-Trp⁴-Lys⁵-Val⁶-Cys⁷)-Thr⁸-NH₂.

HPLC: rt=10.77 min
HRMS (H₂O) m/z=1138.4884 [M+H]⁺ (calc, 1138.4854)
¹H NMR (400 Mhz, D₂O) 0.29-0.40 (m, 1H); 0.42-0.58 (m, 1H); 0.81 (t, J=6.7, 6H); 1.11 (d, J=6.3, 3H); 1.1-1.23 (m, 2H); 1.44-1.55 (m, 1H); 1.9 (s, 3H); 1.95-2.03 (m, 1H); 2.37-2.45 (m, 2H); 2.47-2.62 (m, 2H); 2.65-2.78 (m, 3H); 2.87-2.99 (m, 2H); 3.07-3.2 (m, 2H); 3.8 (dd, J=3.5, J=10.5, 1H); 3.86 (d, J=9.1, 1H); 4.13-4.22 (m, 3H); 4.47 (t, J=7.4, 1H); 4.59-4.78 (m, 2H); 6.69 (d, J=8.4, 2H); 6.94 (d, J=8.4, 2H); 7.03-7.16 (m, 3H); 7.34-7.46 (m, 5H); 7.63 (s, 1H); 7.75-7.8 (m, 3H).

2. Study of the Compounds According to the Invention 2.1 Activity of the Octapeptide Compounds on the Somatostatin Receptors
2.1.1 Protocol for Measurement of the Affinity of the Peptides for the Somatostatin Receptors The affinity of the compounds of the invention for the somatostatin receptors is determined by measurement of the inhibition of the bond of [¹²⁵I-Tyr11]SRIF-14 to membrane preparations of transfected CHO-K1 cells.

The CHO-K1 cells expressing in a stable fashion each of the sub-types of somatostatin receptors are collected with 0.5 mM of EDTA and centrifuged at 500 g for 5 minutes at 4° C. The pellet is re-suspended in phosphate buffer (PBS) and centrifuged at 500 g for 5 minutes at 4° C. The pellet is re-suspended in Tris 50 mM buffer at pH 7.4 and centrifuged at 500 g for 5 minutes at 4° C. The cells are lyzed by sonication and centrifuged at 39,000 g for 10 minutes. The pellet is re-suspended in Tris 50 mM buffer at pH 7.4, an aliquot is removed for assaying the proteins and the remainder is centrifuged at 50,000 g for 10 minutes. The membranes obtained in this last pellet are stored at −80° C.

Measurement of the competitive inhibition of the bond of [$^{125}$I-Tyr11]SRIF-14 (Perkin Elmer) on each of the sub-types of somatostatin receptors is carried out in duplicate in 96-well polypropylene plates. The cell membranes (5 to 20 μg of proteins/well) are incubated with [$^{125}$I-Tyr11]SRIF-14 (0.05 to 0.1 nM) for 50 to 90 minutes at 37° C. (conditions dependent on the sub-type of receptor) in a HEPES buffer medium 50 mM pH 7.4, comprising 0.2% bovine serum albumin (BSA), MgC12 5 mM, Trasylol 200 KIU/mL, Bacitracin 0.02 mg/mL, phenylmethylsulphonyl fluoride 0.02 mg/mL.

The bound [$^{125}$I-Tyr11]SRIF-14 is separated from the free [$^{125}$I-Tyr11]SRIF-14 by filtration through GF/C glass fibre plates (Unifilter, Perkin Elmer) pre-impregnated with 0.1% polyethylenimine (P.E.I.), using a Filtermate 96 (Perkin Elmer). The filters are washed with Tris-HCl buffer 50 mM, pH 7.4 at 4° C. and the radioactivity present is determined using a counter (TopCount, Perkin Elmer).

The data are analyzed by computer-assisted non-linear regression using XLfit 4.2 (IDBS) software.

2.1.2 Results

Examples 1, 2, 3, 4, 5, 6, 7, 8 and 9 have an affinity for the somatostatin receptors sub-type 2 less than or equal to 5 μM.

Examples 1, 2, 3, 4, 6, 7, 8 and 9 have an affinity for the somatostatin receptors sub-type 2 less than or equal to 700 nM.

Examples 1, 2, 3, 8 and 9 have an affinity for the somatostatin receptors sub-type 2 less than or equal to 6 nM.

Examples 1, 2, 3, 4, 5, 6, 8 and 9 have an affinity for the somatostatin receptors sub-type 5 less than or equal to 5 μM.

Examples 1, 2, 3, 8 and 9 have an affinity for the somatostatin receptors sub-type 5 less than or equal to 500 nM.

Examples 3, 8 and 9 have an affinity for the somatostatin receptors sub-type 5 less than or equal to 10 nM.

Examples 1, 2, 3, 4, 5, 8 and 9 have an affinity for the somatostatin receptors sub-type 3 less than or equal to 1 μM.

Examples 2, 3, 8 and 9 have an affinity for the somatostatin receptors sub-type 3 less than or equal to 200 nM.

Examples 8 and 9 have an affinity for the somatostatin receptors sub-type 3 less than or equal to 100 nM.

The invention claimed is:

1. An octapeptide compound of general formula (I)

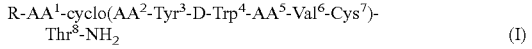

wherein
(i) AA$^1$ represents an amino acid radical linked to the radical R and to the amino acid AA$^2$ according to the formula

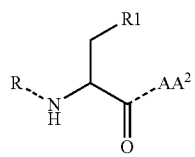

wherein
R1 represents a naphthyl radical optionally substituted by one or more alkyl radicals; and
R represents a hydrogen atom, an alkyl or an acetyl radical;

(ii) AA$^2$ represents an amino acid radical linked to the amino acids AA$^1$ and Tyr$^3$ according to the formula

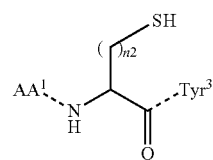

wherein n2 represents an integer ranging from 1 to 2; and
(iii) AA$^5$ represents an amino acid radical linked to the amino acids Trp$^4$ and Val$^6$ according to the formula

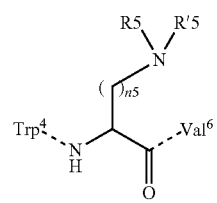

wherein R5 and R'5 represent independently a hydrogen atom, an alkyl or an acetyl radical, and n5 represents an integer ranging from 1 to 6;
and
if AA$^2$ represents a cysteine amino acid radical, then either:
AA$^1$ does not represent a naphthylalanine amino acid radical and AA$^5$ represents a lysine amino acid radical;
AA$^1$ represents a naphthylalanine amino acid radical and AA$^5$ does not represent a lysine amino acid radical; or
AA$^1$ does not represent a radical of naphthylalanine and AA$^5$ does not represent a lysine radical;
or if AA$^2$ does not represent a cysteine radical, then AA$^1$ represents a naphthylalanine amino acid radical and AA$^5$ represents a lysine amino acid radical,
and wherein all the amino acids are in D or L configuration;
or
a pharmaceutically acceptable salt thereof.

2. The octapeptide according to claim 1, wherein n5 represents an integer ranging from 1 to 4.

3. The octapeptide according to claim 1, wherein AA$^2$ represents a cysteine amino acid radical.

4. The octapeptide according to claim 1, wherein AA$^2$ does not represent a cysteine amino acid radical.

5. The octapeptide according to claim 1, wherein AA$^1$ does not represent a naphthylalanine amino acid radical and AA$^5$ represents a lysine amino acid radical.

6. The octapeptide according to claim 1, wherein AA$^1$ represents a naphthylalanine amino acid radical and AA$^5$ does not represent a lysine amino acid radical.

7. The octapeptide according to claim 1, wherein AA$^1$ does not represent a naphthylalanine amino acid radical and AA$^5$ does not represent a lysine amino acid radical.

8. The octapeptide according to claim 1, wherein AA$^1$ represents the amino acid radical of 2-Nal, Ac-2-Nal or CH$_3$-2-Nal.

9. The octapeptide according to claim 1, wherein AA$^2$ represents the amino acid radical of Cys or Hcy.

10. The octapeptide according to claim 1, wherein $AA^5$ represents the amino acid radical of Lys, Lys(Ac), Orn, $(CH_3)_2$Lys, Dab or Dap.

11. The octapeptide according to claim 1, comprising:
H-D-2-Nal$^1$-cyclo(Cys$^2$-Tyr$^3$-D-Trp$^4$-Lys(Ac)$^5$-Val$^6$-Cys$^7$)-Thr$^8$-NH$_2$;
Ac-D-2-Nal$^1$-cyclo(Cys$^2$-Tyr$^3$-D-Trp$^4$-Lys(Ac)$^5$-Val$^6$-Cys$^7$)-Thr$^8$-NH$_2$;
H-D-2-Nal$^1$-cyclo(Cys$^2$-Tyr$^3$-D-Trp$^4$-Orn$^5$-Val$^6$-Cys$^7$)-Thr$^8$-NH$_2$;
H-D-2-Nal$^1$-cyclo(Cys$^2$-Tyr$^3$-D-Trp$^4$-(Me)$_2$Lys$^5$-Val$^6$-Cys$^7$)-Thr$^8$-NH$_2$;
H-D-2-Nal$^1$-cyclo(Hcy$^2$-Tyr$^3$-D-Trp$^4$-Lys$^5$-Val$^6$-Cys$^7$)-Thr$^8$-NH$_2$;
Ac-D-2-Nal$^1$-cyclo(Cys$^2$-Tyr$^3$-D-Trp$^4$-Lys$^5$-Val$^6$-Cys$^7$)-Thr$^8$-NH$_2$;
CH$_3$-D-2-Nal$^1$-cyclo(Cys$^2$-Tyr$^3$-D-Trp$^4$-Lys$^5$-Val$^6$-Cys$^7$)-Thr$^8$-NH$_2$;
H-D-2-Nal$^1$-cyclo(Cys$^2$-Tyr$^3$-D-Trp$^4$-Dab$^5$-Val$^6$-Cys$^7$)-Thr$^8$-NH$_2$; or
H-D-2-Nal$^1$-cyclo(Cys$^2$-Tyr$^3$-D-Trp$^4$-Dap$^5$-Val$^6$-Cys$^7$)-Thr$^8$-NH$_2$;
or a pharmaceutically acceptable salt thereof.

12. The octapeptide according to claim 11, comprising:
H-D-2-Nal$^1$-cyclo(Cys$^2$-Tyr$^3$-D-Trp$^4$-Orn$^5$-Val$^6$-Cys$^7$)-Thr$^8$-NH$_2$;
H-D-2-Nal$^1$-cyclo(Cys$^2$-Tyr$^3$-D-Trp$^4$-(Me)$_2$Lys$^5$-Val$^6$-Cys$^7$)-Thr$^8$-NH$_2$;
H-D-2-Nal$^1$-cyclo(Hcy$^2$-Tyr$^3$-D-Trp$^4$-Lys$^5$-Val$^6$-Cys$^7$)-Thr$^8$-NH$_2$; or
Ac-D-2-Nal$^1$-cyclo(Cys$^2$-Tyr$^3$-D-Trp$^4$-Lys$^5$-Val$^6$-Cys$^7$)-Thr$^8$-NH$_2$;
or a pharmaceutically acceptable salt thereof.

13. The octapeptide according to claim 12, comprising:
H-D-2-Nal$^1$-cyclo(Hcy$^2$-Tyr$^3$-D-Trp$^4$-Lys$^5$-Val$^6$-Cys$^7$)-Thr$^8$-NH$_2$ or
a pharmaceutically acceptable salt thereof.

14. A medicament comprising a compound according to claim 1 and at least one pharmaceutically acceptable carrier.

15. A composition comprising a compound according to claim 1, as active ingredient in combination with at least one pharmaceutically acceptable excipient.

16. A method of treating a pathological state or disease related to a growth hormone, comprising administering an effective amount of the octapeptide of claim 1 in a subject in need thereof.

17. The method according to claim 16, wherein the octapeptide binds to a somatostatin receptor.

18. A method of treating a pathological state or disease related to a growth hormone, comprising administering the composition of claim 15.

* * * * *